US00PP10801P

United States Patent [19]

Nagase

[11] Patent Number: Plant 10,801

[45] Date of Patent: Feb. 23, 1999

[54] VERBENA PLANT NAMED 'SUNMARIBA'

[75] Inventor: Yuki Nagase, Seki, Japan

[73] Assignee: Suntory Limited, Osaka, Japan

[21] Appl. No.: 756,814

[22] Filed: Nov. 26, 1996

[51] Int. Cl.[6] ..... A01H 5/00

[52] U.S. Cl. ..... Plt./87

[58] Field of Search ..... Plt./87

[56] References Cited

U.S. PATENT DOCUMENTS

| | | | |
|---|---|---|---|
| P.P. 2,537 | 6/1965 | Fujii | Plt./87 |
| P.P. 8,995 | 11/1994 | Tachibana et al. | Plt./87 |
| P.P. 9,014 | 12/1994 | Tachibana et al. | Plt./87 |
| P.P. 9,059 | 2/1995 | Tachibana et al. | Plt./87 |
| P.P. 9,085 | 3/1995 | Tachibana et al. | Plt./87 |
| P.P. 9,121 | 4/1995 | Tachibana et al. | Plt./87 |
| P.P. 9,411 | 12/1995 | Tachibana et al. | Plt./87 |

*Primary Examiner*—Howard J. Locker

*Attorney, Agent, or Firm*—Burns, Doane, Swecker & Mathis, L.L.P.

[57] ABSTRACT

A new and distinct verbena variety is provided which forms attractive large vivid reddish purple blossoms. The plant is broad and exhibits a spreading growth habit. The blossoms are borne in abundance on spikes. The blossoming is of long duration and commonly occurs between April and November. The plant exhibits a high tolerance to rain, cold, and heat. Good resistance to diseases, such as powdery mildew, also is exhibited.

2 Drawing Sheets

BACKGROUND OF THE VARIETY

The present invention relates to a new and distinct variety of verbena plant obtained from a crossing "Novaris deep blue with eye" (♀) and a wild type of verbena plant, *Verbena peruviana* (♂) native to Brazil.

The verbena is a very popular plant and is used for flower bedding and potting in the summer season. There are only a few varieties of the verbena plant which have a spreading growth habit, much branching, the formation of a high number of flowers in a spike and which have a high resistance to rain, heat, cold, and diseases. Accordingly, this invention was aimed at obtaining a new variety having a spreading growth habit, strongly branching, the formation of a high number of flowers in a spike, a large diameter flower, high tolerance to heat and cold, and resistance to diseases and pests, and also having vivid reddish purple flower petals.

The new variety of Verbena plant according to this invention originated from crossing *verbena hybrida* "Novaris deep blue with eye" (♀) and a wild type of verbena plant *Verbena peruviana* (♂) native to Brazil. The new variety of the present invention is botanically classified Verbena hybrida.

First of all, 74 seedlings were obtained in the autumn of 1992, from crossing "Novaris deep blue with eye" as female parent and a wild type of verbena plant (*Verbena peruviana* f. rosea) as pollen parent in the May of 1992. From this crossing, 28 seedlings were selected in view of spreading growth habit were propagated by cuttings, and then grown as a trial for flower bedding and planter growth beginning in the spring of 1993. Finally only one plant was selected from these 28 during such evaluation that was carried out until the autumn of 1994 and the botanical characteristics of 28 seedlings were examined, using the similar variety "Novaris deep blue with eye" for comparison. As a result, it was concluded that this verbena is distinguishable from any other variety whose existence is known to us, is uniform and is stable in its characteristics. This new variety of verbena plant was named "Sunmariba".

In the following description, the color-coding is in accordance with the Horticultural Colour Chart of The Royal Horticultural Society, London, England (R.H.S. Colour Chart), and the Inter-Society Colour Council-Nation Bureau of Standard Color Name (I.S.C.C.-N.B.S. Color Name). A color chart based on The Japan Color Standard for Horticultural Plant (J.H.S. Color Chart) is also added for reference.

The "Novaris deep blue with eye" plant used in the crossing as female parent variety is commercially available. The main botanical characteristics of "Novaris deep blue with eye" are as follows.

Plant:
- *Growth habit.*—Erect.
- *Plant height.*—20–30 cm.
- *Plant extension.*—15–20 cm.

Stem:
- *Diameter.*—2.0–3.0 mm.
- *Anthocyanin pigmentation.*—Absent.
- *Branching.*—Medium.
- *Pubescence.*—Medium.
- *Length of internode.*—3.0–4.0 cm.

Leaf:
- *Phyllotaxis.*—Opposite.
- *Shape of blade.*—Hastate.
- *Length.*—3.0–4.0 cm.
- *Width.*—2.0–2.5 cm.
- *Depth of incision.*—Shallow.
- *Color.*—Dark yellow green (R.H.S. 146A, JHS 3508)
- *Pubescence.*—Few.

Flower:
- *Facing direction.*—Upward.
- *Outward curvature of petal.*—Slightly curved.
- *Diameter.*—1.5–2.0 cm.
- *Height.*—20–30 mm.
- *Color.*—Dark purple (R.H.S. 86A, JHS 8609).
- *Color intensity.*—Absent.
- *Overlapping of petals.*—Opened.
- *Spike.*—30–40 mm in length: and 40–50 mm in diameter.
- *Calxy.*—1.0–1.5 cm in length.
- *Anthocyanin pigmentation of calyx limb.*—Absent.
- *Peduncle.*—2–3 mm in thickness; and 50–60 cm in length.

*Number of flowers.*—Medium (commonly 10–14).
*Reproductive organs.*—1 pistil and 4 stamens.
*Flower fragrance.*—Absent.
*Flowering duration.*—Long.

Physiological and ecological characteristics: Low resistance to diseases and pests, low tolerances to heat and cold.

The pollen parent used in the obtaining of this new variety "Sunmariba" was a wild type of verbena native to South Brazil (*Verbena peruviana*). This wild type of verbena plant is presently maintained at the Plant Biotechnology Laboratory of Suntory Ltd., residing at 863-1, Aza-Iketani, Oomori-cho, Youkaiti-shi, Shiga-ken, Japan. . The main botanical characteristics of this pollen parent are as follows.

Plant:
*Growth habit.*—Spreading.
*Plant height.*—10–20 cm.
*Plant extension.*—100–150 cm.

Stem:
*Diameter.*—1.0–2.0 mm.
*Anthocyanin pigmentation.*—Present.
*Branching.*—Medium.
*Pubescence.*—Medium.
*Length of internode.*—3.0–4.0 cm.

Leaf:
*Phyllotaxis.*—Opposite.
*Shape of blade.*—Hastate.
*Length.*—3.0–4.0 cm.
*Width.*—1.5–2.0 cm.
*Depth of incision.*—Shallow.
*Color.*—Moderate olive green (R.H.S. 146A, JHS 3509)
*Pubescence*—Few.

Flower:
*Facing direction.*—Upward.
*Outward curvature of petal.*—Slightly curved.
*Diameter.*—2.0–3.0 cm.
*Height.*—20–30 mm.
*Color.*—Strong reddish purple (R.H.S. 77B, JHS 8911).
*Color intensity.*—Absent.
*Overlapping of petals.*—Opened.
*Spike.*—30–40 mm in length; and 50–60 mm in diameter.
*Calyx.*—1.5–2.0 cm in length.
*Anthocyanin pigmentation of calyx limb.*—Absent.
*Peduncle.*—1–2 mm in thickness; and 3.0–5.0 cm in length.
*Number of flowers.*—Plentiful (commonly 10–14)
*Reproductive organs.*—1 pistil and 4 stamens.
*Flower fragrance.*—Absent.
*Flowering duration.*—Short.

Physiological and ecological characteristics: High resistance to diseases and pests, high tolerances to heat and cold.

This new variety of verbena plant "Sunmariba" was asexually reproduced by cuttings at the Plant Biotechnology Laboratory of Suntory Ltd., 863-1, Aza-Ikentani, Oomori-cho, Youkaiti-shi, Shiga-ken, Japan, and the homogeneity and stability thereof were confirmed.

SUMMARY OF THE VARIETY

This new variety of verbena plant has spreading growth habit having long stems. A broad plant is formed. The plant has abundant branching and an abundant number of flowers in a spike, with a great profusion of blooms. The Blooming period is from late April to November and the flowering duration is long. The entire bush remains in bloom for a considerable period of time. The flower size is large and the petal coloration of the flowers is vivid reddish purple. The plant is highly tolerant to cold and heat, exhibits a high resistance to pests and diseases, is particularly resistant to powdery mildew and rain.

DESCRIPTION OF THE VARIETY

Figure 1:
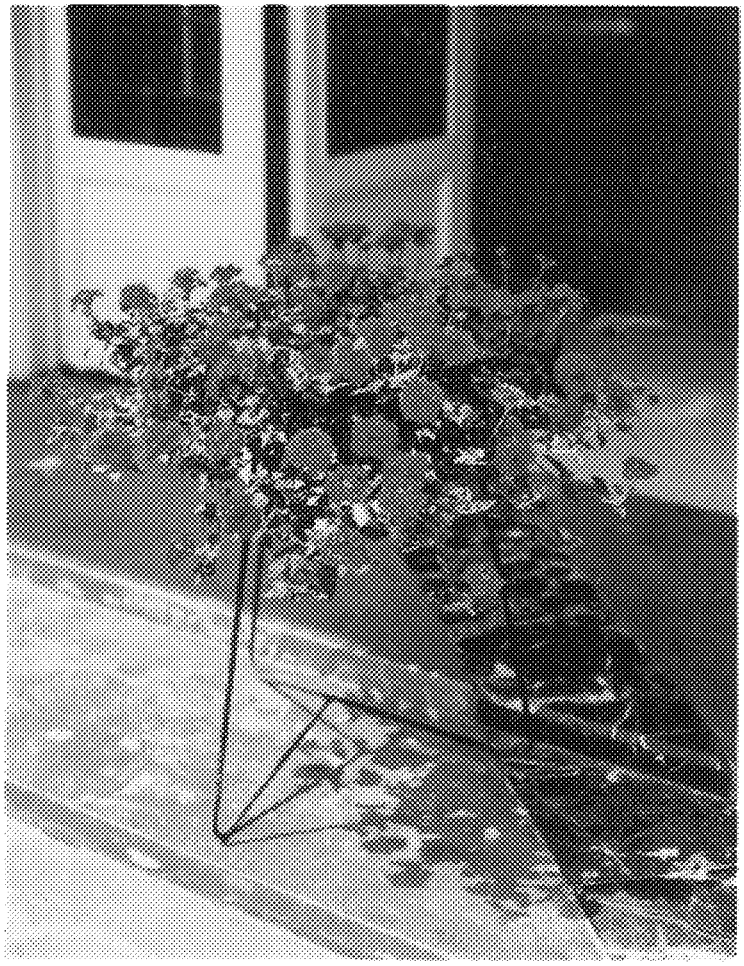
FIG. 1 is photograph giving a partial view of the new variety of verbena plant while planted in a flower pot.
Figure 2:
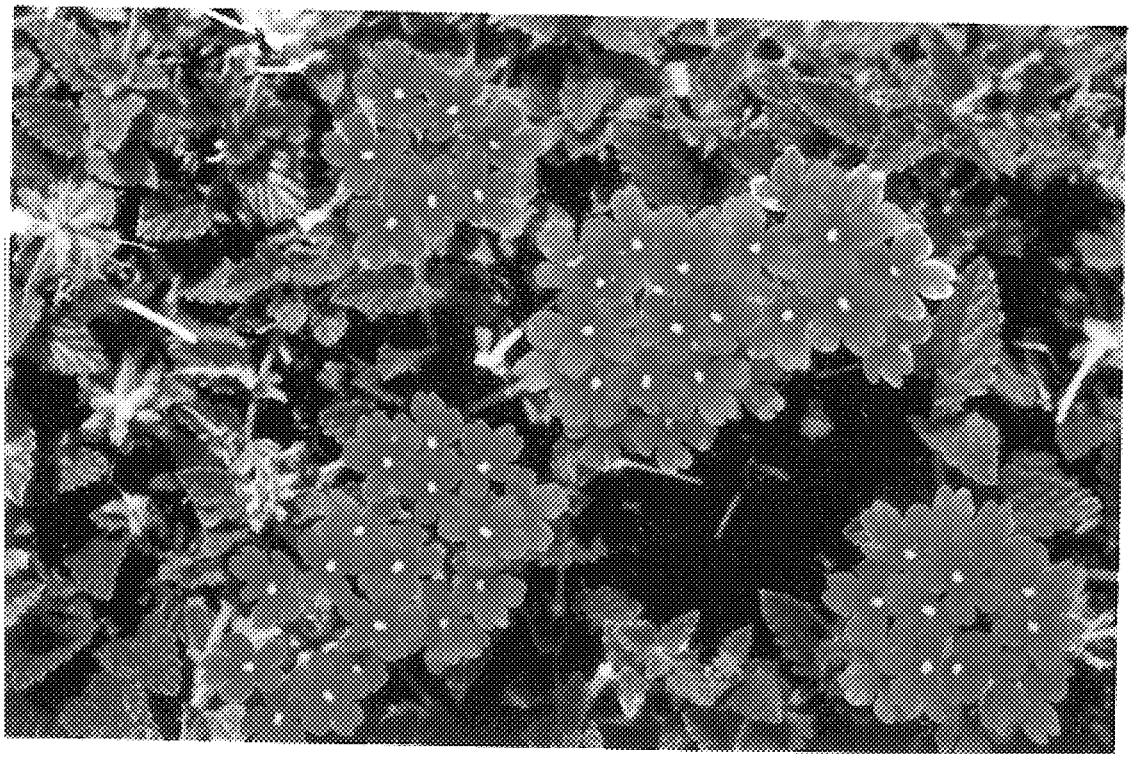
FIG. 2 is a photograph of the flowers of the new variety of verbena plant.

The botanical characteristics of the new and distinct variety of verbena plant, "Sunmariba" are as follows.

Plant:
*Growth habit.*—Spreading.
*Plant height.*—10–20 cm.
*Plant extension.*—60–80 cm.
*Growth.*—Very vigorous with abundant branching and a great profusion of blooms; and with the whole bush remaining in bloom for considerable period of time.

Stem:
*Diameter.*—3.0–4.0 mm.
*Anthocyanin pigmentation.*—Present.
*Branching.*—Abundant.
*Pubescence.*—Medium.
*Length of internode.*—2.0–4.0 cm.

Leaf:
*Phyllotaxis.*—Opposite.
*Shape of blade.*—Hastate.
*Length.*—4.0–5.0 cm.
*Width.*—2.0–3.0 cm.
*Depth of incision.*—Shallow.
*Color.*—Dark yellow green (R.H.S. 146A, JHS 3508).
*Pubescence.*—Few.

Flower:
*Facing direction.*—Upward.
*Outward curvature of petal.*—Slightly curved.
*Diameter.*—1.5–2.0 cm.
*Height.*—20–30 mm.
*Color.*—Vivid reddish purple (R.H.S.0A, JHS 8906) on the upper side of the open petals, brilliant purple (R.H.S. 75A, JHS 8604) on the under side of the open petals, purplish white (R.H.S. 69D, JHS 8601) on the corolla throat, and pale yellow green and almost white (R.H.S. 1D, JHS 3102) at the corolla eye area.
*Overlapping of petals.*—Opened.
*Spike.*—30–50 mm in length: and 40–60 mm in diameter.
*Calyx.*—1.0–2.0 cm in length.
*Anthocyanin pigmentation of calyx limb.*—Absent.
*Peduncle.*—1–2 mm in thickness; and 4.0–5.0 cm in length.
*Number of flowers.*—Plentiful (commonly 13–17).
*Reproductive organs.*—1 pistil and 4 stamens.
*Flower fragrance.*—Absent.
*Flowering duration.*—Long.

Physiological and ecological characteristics: High resistance to diseases and pests, particularly to powdery mildew. High tolerance to heat and cold is exhibited. High tolerance to rain is exhibited. Upon self-pollination viable seed forms on the plant of the new variety of the present invention. However, such seed does not form plants identical to the new variety since the new variety is an $F_1$ hybrid. Pinching of the blossoms is not necessary to ensure continued blooming. It is found that such pinching will increase the number of blooms that are formed.

This new variety of verbena plant is most suitable for growing as flower bedding and as pot plant in planters, and is further particularly well suited for growing as a ground cover.

The plant of this new variety, "Sunmariba" is presently planted and maintained at the Plant Biotechnology Laboratory of Suntory Ltd., 863-1, Aza-Iketani, Oomori-cho, Youkaiti-shi, Shiga-ken, Japan.

When the new variety of the present invention is compared to the 'Royal Carpet' variety (U.S. Plant Pat. No. 2,537), it is found that the new variety exhibits a more consistent vivid reddish purple blossom coloration whereas the 'Royal Carpet' blossoms increase in color intensity towards the center and become more reddish in appearance. The corolla eye of new variety is a pale yellow green (i.e., almost white), as indicated, while the corolla eye of 'Royal Carpet' variety is uranium green.

I claim:

1. A new and distinct variety of verbena plant having the following combination of characteristics:

(a) exhibits a spreading growth habit with long stems,
(b) forms in abundance on spikes attractive large vivid reddish purple blossoms over an extended period of time,
(c) exhibits a high tolerance to rain, cold and heat, and
(d) exhibits good resistance to powdery mildew;

substantially as illustrated and described.

* * * * *

SUNMARIBA

SUNMARIBA